United States Patent [19]

Czekajewski et al.

[11] Patent Number: 4,947,339
[45] Date of Patent: Aug. 7, 1990

[54] METHOD AND APPARATUS FOR MEASURING RESPIRATION, OXIDATION AND SIMILAR INTERACTING BETWEEN A SAMPLE AND A SELECTED COMPONENT OF A FLUID MEDIUM

[75] Inventors: Jan Czekajewski, 4348 Shire Cove Rd., Columbus, Ohio 43220; Leif B. Nennerfelt, Galloway, Ohio

[73] Assignee: Jan Czekajewski, Columbus, Ohio

[21] Appl. No.: 278,599

[22] Filed: Dec. 1, 1988

[51] Int. Cl.$^5$ .................. G06F 15/46; G01N 31/00
[52] U.S. Cl. ........................ 364/497; 364/571.01; 73/863.02; 73/863.71; 422/82.13; 422/82.12; 422/82.01; 422/82.09
[58] Field of Search .............. 364/497, 499, 571.01; 73/863.01, 863.02, 863.03, 863.21, 863.71; 422/68, 62

[56] References Cited

U.S. PATENT DOCUMENTS

| | | | |
|---|---|---|---|
| 3,313,157 | 4/1967 | Gilson | 73/401 |
| 3,740,320 | 6/1973 | Arthur | 195/103.5 R |
| 3,942,792 | 3/1976 | Topol | 273/19 |
| 4,335,438 | 6/1982 | Smolen | 364/497 |
| 4,384,925 | 5/1983 | Stetter et al. | 364/497 |
| 4,520,654 | 6/1985 | Terhune | 364/497 |
| 4,638,444 | 1/1987 | Laragione et al. | 364/497 |
| 4,744,037 | 5/1988 | Niina et al. | 364/497 |
| 4,766,550 | 8/1988 | Byers et al. | 364/497 |

FOREIGN PATENT DOCUMENTS

2049182A 12/1988 United Kingdom.

Primary Examiner—Parshotam S. Lall
Assistant Examiner—Brian M. Mattson
Attorney, Agent, or Firm—Porter, Wright, Morris & Arthur

[57] ABSTRACT

Atmospheric air is introduced into reference and sample chambers, whereupon alternating circulation of the gases in the two chambers through a carbon dioxide sensor, an oxygen sensor, a pressure sensor and a pressure regulator occurs before the gases are returned to their respective chambers. The calculation of rate of production or consumption of carbon dioxide and oxygen by a tissue or other sample in the sample chamber is controlled by a microprocessor which receives signals from the carbon dioxide, oxygen and pressure sensors and controls the circulation of the gases. Sensor drift is compensated for in the calculation through the use of multiple reference chamber readings and through volume determinations for the reference and sample chambers and the sensors.

14 Claims, 2 Drawing Sheets

METHOD AND APPARATUS FOR MEASURING RESPIRATION, OXIDATION AND SIMILAR INTERACTING BETWEEN A SAMPLE AND A SELECTED COMPONENT OF A FLUID MEDIUM

BACKGROUND OF THE INVENTION

The present invention relates to instruments and to methods of measuring low levels of consumption and production of certain components, typically oxygen and carbon dioxide, in a fluid medium, such as air, by plant and animal tissues, cell cultures, synthetic resins and metals. More particularly, the present invention relates to such instruments and methods which compensate for interfering factors, such as sensor drift and pressure/temperature fluctuations.

The measurement of oxygen consumption and carbon dioxide production is applied in several fields. In entomology, such measurements are helpful in determining insect food sources. In the perishable food industry, respiration measurements are used to evaluate means of retarding ripening. Another application is in measuring the biological activity of bacterial cultures, sludge, and other hazardous organic materials. Respirometers are also used to measure oxidation of metals and oxygen uptake by synthetic resins during polymerization.

Various methods and instruments have been used in the past to measure low levels of respiratory gas exchange. Oxygen consumption is commonly determined by measuring changes in the volume of gas in a chamber as oxygen is consumed by the tissue or other sample. The Warburg apparatus, a relatively well known example of such a volumetric device, employs a solution of potassium hydroxide in the sample chamber to absorb carbon dioxide produced by the sample. The change in the volume of the air in the sample chamber is measured by a manometric tube which is connected to the sample chamber on one end and is open to the atmosphere on the other end. Oxygen consumption is assumed to be the sole source of air volume change within the sample chamber. This assumption, however, is unreliable because other factors, such as the temperature of the sample chamber and the barometric pressure, can change its air volume. Such temperature-induced air volume changes can be minimized by placing the apparatus in a temperature-controlled water bath, but even the best water baths cannot regulate the temperature precisely enough for the present low-level respiration applications.

Differential volumetric respirometers, such as the apparatus disclosed in U.S. Pat. No. 3,313,157 to Gilson, seek to improve upon the Warburg apparatus. The adverse effects of temperature changes are offset by employing a reference chamber substantially equal in volume to the sample chamber, under the principal that any temperature change affects the volumes of the gases in the two chambers equally. Oxygen consumption is measured by the difference between the volume changes in the two chambers. However, the assumption that the temperatures of the chambers are the same is unreliable if the sample generates it own heat, as is likely in oxidative reactions.

The Warburg and differential volumetric respirometers also lack the capacity to easily measure carbon dioxide production. Such knowledge is important in many metabolic measurements, since the carbon dioxide production rate is used together with the oxygen consumption rate to compute a respiratory quotient which indicates what foodstuff is being metabolized. In the Warburg device, carbon dioxide production can be determined only by chemical analysis of the potassium hydroxide solution which presumably absorbs the entire output of this gas. Accurate chemical analysis is difficult and time consuming, and only a single determination can be made at the end of the study. Also, in plants, carbon dioxide is consumed, rather than produced, and carbon dioxide consumption cannot be measured using this technique.

Closed respirometers which employ gas analyzers to measure consumption and production of specific gases are also known in the art. Gas analyzers, however, often fluctuate or drift as a result of environmental influences, such as pressure and temperature changes. Typically, drift in the gas analyzer is corrected by manual recalibration of the sensor using a known reference gas prior to each sample gas measurement. However, U.K. Patent No. 2049192A to Austin et al. discloses a differential-type carbon dioxide analyzer in which an infrared beam is alternately directed through a first cell containing a sample gas and a second cell containing a reference gas. The Austin et al. device produces an output signal proportional to the difference between the signals produced after passage of the two beams through the two analyzer cells. To a degree, the Austin et al. respirometer corrects for drift in the gas analyzers, but it has limited applicability because the infrared absorption device it employs cannot detect many other gases, such as oxygen. Furthermore, the Austin et al. device does not fully compensate for sample-induced sensor drift. For example, gas pressure and content variations in the sample cell caused by water vapor from the sample would not be found in the reference cell. Hence, the output signal would not compensate for such drift.

Thus, the present inventors were faced with the problems of accurately measuring changes in the composition of a multi-component fluid medium resulting from low levels of respiration or oxidation while accounting for variables, such as temperature and pressure changes, within the system.

SUMMARY OF THE INVENTION

An apparatus according to the present invention for measuring respiration, oxidation and similar interactions between a sample and a selected component of a fluid medium basically comprises: a reference chamber adapted to house a first quantity of a reference fluid medium; a sample chamber adapted to house a sample and a second quantity of the reference fluid medium and wherein the selected component in the second quantity of the reference fluid medium interacts with the sample to define a sample fluid medium; a sensor which generates a plurality of reference and sample signals, each of these signals being generally indicative of a relative quantity of the selected component within the reference and sample fluid media, respectively; equipment for alternately circulating the reference and sample fluid media from their respective chambers to the sensor and back to their respective chambers; and a processor adapted to receive at least two reference signals and at least two sample signals and to calculate the interaction between the sample and the selected component in accordance with a formula which employs at least the two reference signals to compensate for that portion of the reference and sample signals which is indicative of a factor other than the relative quantity of the selected component.

A method according to the present invention basically comprises introducing a first quantity of the reference fluid medium into the reference chamber; introducing a sample into the sample chamber; introducing a second quantity of the reference fluid medium into the sample chamber for interaction between the sample and a selected component of the second quantity of the reference fluid medium, thereby defining a sample fluid medium; alternately circulating the reference and sample fluid media from their respective chambers to the sensor and back to their respective chambers; generating a plurality of reference and sample signals with the sensor, each of the signals being generally indicative of a relative quantity of the selected component within the reference and sample fluid media, respectively; and calculating in a processor the interaction between the sample and the selected component with at least two sample signals and at least two reference signals in accordance with a formula which employs at least two reference signals to compensate for that portion of the reference and sample signals which is (are) indicative of a factor other than the relative quantity of the selected component.

DETAILED DESCRIPTION OF THE PREFERRED EMBODIMENT

Figure 1:
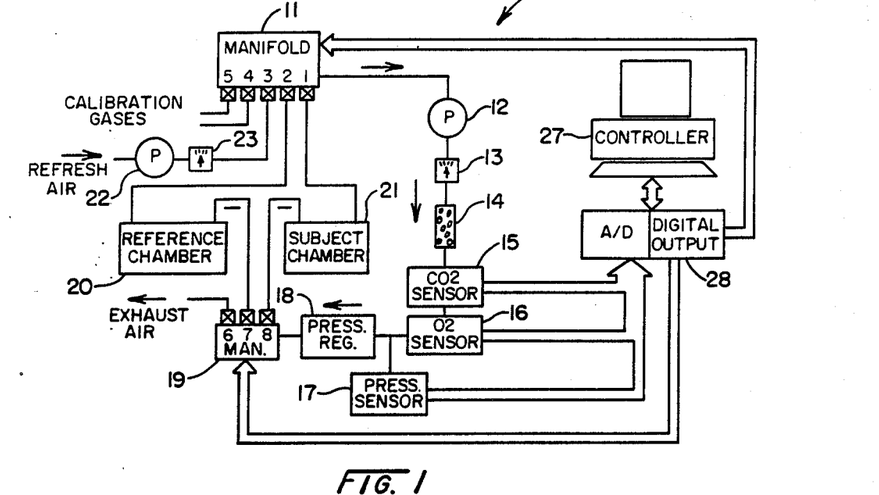
FIG. 1 is a diagram of the components of a respirometer embodying the present invention.

As illustrated in FIG. 1, a respirometer, generally designated 10, according to the present invention includes the following components connected together by tubing or other conduits adapted to transport fluid media, particularly gases: a first manifold 11 which includes valves 1–5, a pump 12, a flow meter and flow regulator 13, a dehumidifier 14, a carbon dioxide analyzer 15, an oxygen analyzer 16, a pressure sensor 17, a pressure regulator 18, an exhaust manifold 19 which includes valves 6–8, a reference chamber 20 connected between valve 2 on the intake manifold 11 and valve 7 on the exhaust manifold 19, and a sample chamber 21 connected between valve 1 on the intake manifold and valve 8 on the exhaust manifold The circulating pump 12 alternately circulates a reference fluid medium, typically air, between the reference chamber 20 and the gas analyzers 15, 16 and a sample fluid medium, resulting from an interaction between a sample, such as plant tissue, and selected components, i.e. oxygen and carbon dioxide, in the second quantity of the reference fluid medium, between the sample chamber 21 and the analyzers 15, 16. The circulating pump 12 is intended to provide a steady output flow, since many gas analyzers are sensitive to the flow rate of the gas passing through them. If the pump changes speed, back pressure behind the flow regulator 13 will probably change, and, hence, the flow rate is likely to be altered. The aforesaid pump 12 is also intended to be sealed completely from the outside air and may be a small diaphragm pump capable of delivering up to 1 liter/minute. In this regard, it may be noted that pressure changes arising from within the system should be minimized. Internal pressure fluctuation may be generated from two sources: variations in pump output and changes in humidity. There are pressure drops within the tubing due to its inherent resistance to flow, as well as at the component connections. As pump output fluctuates, the pressure drops change, so the pressure at the oxygen sensor changes. To minimize this problem, constrictions in the fluid passages should be avoided. Furthermore, since the ambient air pressure fluctuates, the system should be sealed from the outside. Leaks in the system or soft tubing should be avoided since they would allow external pressure changes to be transmitted into the system.

Valves 4 and 5 on the intake manifold 11 are provided for connection to calibration gases. Typically, the reference fluid medium is atmospheric air. The air in the system may be replaced by providing a fresh air pump 22 with a suitable regulator 23 in fluid communication with the system via valve 3 on intake manifold 11. Valve 6 on the exhaust manifold 19 permits the system to be vented whenever calibration gas or fresh air is being introduced. By opening valves 1 and 2 on the intake manifold 11 and valves 7 and 8 on the exhaust manifold 19, the reference and sample chambers 20 and 21, respectively, and the other components in fluid communication therewith, may be flushed with outside air by operation of the fresh air pump 22.

The flow meter/flow regulator 13 is intended to permit at least a crude flow measurement and regulation of the circulating fluid media in the system. A rotameter with a built-in control valve is suitable. In this manner, the pump 12 is assisted in providing a steady flow rate. The built-in control valve is preferably a metering (needle) valve and likewise controls the rate of flow of the various fluid media to the sensors 15 and 16.

The air drier or dehumidifier 14 comprises a sealed container which is filled with a desiccant, such as granular anhydrous calcium chloride. Calcium chloride is the preferred desiccant since it does not absorb or give off oxygen or carbon dioxide.

The carbon dioxide analyzer 15 measures the concentration or fraction of carbon dioxide in the various fluid media passing through it and produces a signal voltage which reflects this carbon dioxide fraction. Preferably, the aforesaid analyzer 15 is of the infrared absorption type.

The oxygen analyzer 16 measures the concentration or fraction of oxygen in the various fluid media passing through it and produces a signal voltage which reflects this oxygen fraction. Preferably, an electro-chemical fuel cell or a paramagnetic oxygen analyzer is employed.

As previously indicated, gas analyzers, such as the above, are typically sensitive to pressure changes in the fluid medium passing therethrough and are likely to give incorrect readings due to such pressure fluctuations. Variations in humidity within the system are one cause of such pressure changes. For instance, when a wet sample is placed in the sample chamber 21, the humidity in the sample chamber rises and, since the system is closed, the pressure rises as well. The humidity level, and hence, the pressure will fluctuate substantially in the system as the reference and sample fluid media are alternately circulated through the respirometer unless some stabilizing mechanism is provided. When the reference fluid medium is being analyzed, the sample fluid medium in the sample chamber 21, is still, and its humidity rises. When the sample fluid medium is being circulated, it passes through the drier 14, thereby causing its water content to fall. The resulting pressure fluctuations can cause significant errors.

Figure 3:
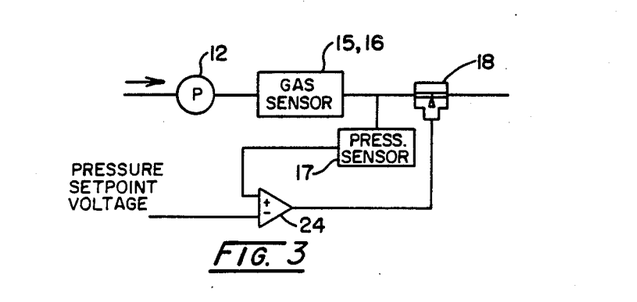
FIG. 3 is a diagram of the preferred means of regulating the pressure of the fluid media in the sensors.

A variety of means may be used to reduce pressure fluctuations due to humidity changes. Such pressure variation is preferably stabilized by measuring the pressure in the gas analyzers and using a mechanism to counteract variations in this value. As indicated in FIG. 3, the preferred components include a pressure indicator 17 which measures the pressure of the fluid medium within or immediately downstream of the gas analyzers 20 and an electrically controlled pressure regulator 18 having a valve with a variable orifice downstream of the gas analyzers. The pressure indicator 17 is preferably a transducer that produces a voltage which varies in relation to the pressure in the gas sensors 15, 16. A comparator 24 either increases the voltage supplied to the valve 18 when the voltage produced by the transducer 17 exceeds a set point voltage, thereby increasing the valve opening and reducing the pressure, or the comparator 24 decreases the voltage supplied to the valve 18 when the voltage produced by the transducer 17 falls below the set point voltage, thereby reducing the valve opening and increasing the pressure in the sensors. The pressure in the sensors is thereby maintained at or around the desired set point.

Alternatively, the electrically actuated variable valve 18 may be replaced with a variable speed pump (not shown). The speed of this variable pump relative to the circulating pump 12 determines the pressure between them. If the variable speed pump runs faster, the pressure will fall and vice versa. Another alternative to using the electrically actuated valve 18 is to place a heating element (not shown) inside the reference chamber or jar 20. The heating element can be used to change the temperature of the fluid medium inside the reference chamber, thereby causing it to expand or contract. By varying the current through the heating element, the pressure in the system can be modulated to compensate for humidity-induced changes. If the pressure sensor 17 detects an increase, the current through the heating element would be lowered, and if the sensor detects a decrease, the heating element current would be increased. Another possible method for reducing pressure fluctuations would be to introduce a small leak in the system to the outside, thereby causing pressure changes in the system to be vented to the outside. Although the outside air pressure also fluctuates, it is somewhat more stable than the pressure inside the system when water is present inside the subject chamber 21. Furthermore, the leak could be made very small so that sharp pressure changes in the outside air due to opening and closing doors, air currents and the like would not be transmitted into the system. Yet another means of stabilizing the pressure inside the system could include a large, empty, rigid container attached to the system. The container would allow gas volume changes in the system due to changes in humidity to be spread over a larger volume, thereby reducing pressure changes. For instance, adding a 10 liter container to the system having an original volume of 2 liters would reduce the pressure fluctuations to 1/6th of the unregulated amount. To a certain extent, the use of such a container would change the oxygen and carbon dioxide gas fractions; however, by connecting the container to the system through a long, thin tube, the exchange of gas between the system and the container would be minimized.

The following is a description of the method used to measure the rate of change in the oxygen and carbon dioxide content of the sample fluid medium. Prior to starting the measurement, the reference chamber 20 and sample chamber 21 are flushed with the reference fluid medium, preferably fresh air, by opening valves 1-3 in the intake manifold 11, opening valves 6-8 in the exhaust manifold, and engaging the fresh air pump 22. In this manner, the entire system, including the gas sensors 15, 16 are flushed with fresh air. The fresh air pump 22 preferably forces air into the system at a rate much higher than the pumping rate of the circulating pump 12. The flushing period lasts sufficiently long for the volume of the system to be flushed several times. Flushing the system is important because, absent a fresh fluid medium, respiration of a sample can become so great that the carbon dioxide and oxygen fractions of the sample fluid medium reach a level of imbalance which causes abnormal respiration to occur.

Typically, the sample is introduced into the sample chamber 21 prior to flushing with the reference gas, i.e. ambient air. After the flushing interval, a settling period of approximately 4 minutes is provided to permit the gas sensors 15, 16 to stabilize.

Figure 2:
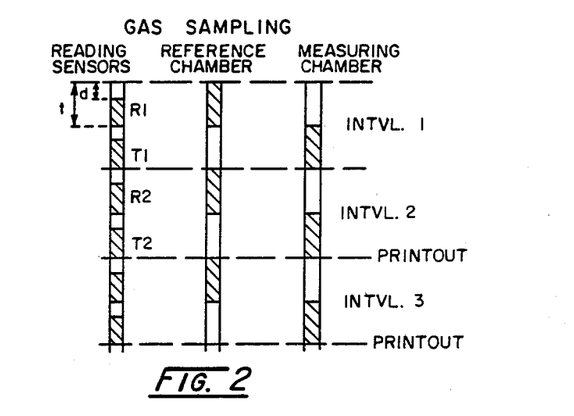
FIG. 2 is a diagram of the timing sequence for circulating the fluid media in the reference and sample chamber and for reading the sensors.

Next, the air in the reference chamber 20, i.e. the reference fluid medium, is analyzed. Valves 2 and 7 are opened, and the reference gas is pumped through the drier 14, sensors 15, 16, and back to the reference chamber 20. As indicated in FIG. 2, the reference gas is preferably circulated in this manner for a period of time equal to one half of a testing interval. Next, the sample fluid medium in the sample chamber 21 is analyzed. The sample gas results from the respiration or other interaction of the sample with the selected components, i.e. oxygen and carbon dioxide, in the air provided to the sample chamber during flushing. Valves 1 and 8 are opened, and the sample fluid medium is pumped through the drier and sensors and back to the sample chamber and is circulated through the system in this manner for a period of time equal to one half of the testing interval.

As further indicated in FIG. 2, the reference fluid medium and the sample fluid medium are alternately circulated through the system for the duration of the experiment. Inevitably, some mixing of the reference and sample gases occurs. Mixing of the reference and sample gases complicates the matter of compensating for drift, i.e. variation in sensor readings due to factors other than changes in the composition of the gas being analyzed, since the composition of the reference gas does not remain completely constant. Such mixing may be compensated for during the calculation of the oxygen consumption and carbon dioxide production rates in the manner described below in some detail. Basically, however, by calculating the various volumes within the system, the amount of mixing between the reference and sample gases may be quantified.

Measurement of the volume of the sample chamber 21 and the sensors 15 and 16 preferably proceeds as follows. Basically, volume measurement is done by measuring the pressure changes in different sections of the system as they are pressurized in isolation and then connected together. To measure the sensor volume ($V_S$), the following procedure is executed. First, the pressures in the sensors and the reference and sample chambers are allowed to equalize with the outside air pressure by opening valves 6–8 and leaving the other valves closed. This first pressure ($P_A$) in the system is recorded and then all valves are closed. Next, a second pressure ($P_S$) is established in the sensors by opening valve 5 to one of the calibration gases and monitoring the p pressure in the sensors as the pressure increases. Pressure sensor 17 (FIG. 1) is employed for this purpose. When the pressure reaches a preset level, preferably 900 mmHg, valve 5 is closed and the second pressure ($P_S$) in the sensors is recorded. Next, valve 7 is opened, and the second pressure in the sensors is allowed to equalize with the first pressure in the reference chamber 20 to establish a third pressure ($P_T$).

The volume of the sensors ($V_S$), which includes the volumes of the conduits and components disposed between the pump 12 and the reference chamber 20, is calculated using the values determined in the forgoing manner, as well as a known value ($V_R$) for the reference chamber volume, and in accordance with the following formula:

$$V_S = V_R / [(P_S - P_A)/(P_T - P_A) - 1]$$

To measure the net volume ($V_T$) of the sample chamber 21, the volume of the sample must be accounted for. To do so, the pressure in the reference and sample chambers and in the sensor is allowed to equalize with atmospheric pressure ($P_A$) as described above. Then, a fourth pressure ($P_{RS}$) is established in the reference chamber and the sensors by opening valves 5 and 7 and pumping in a calibration gas. When the fourth pressure ($P_{RS}$) reaches a preset level substantially higher than the first pressure ($P_A$), valve 5 is closed. Next, valve 8 is opened and the first pressure in the sample chamber is allowed to equalize with the fourth pressure in the sensors and the reference chamber to establish a fifth pressure ($P_C$). The net volume ($V_T$) of the sample chamber may then be determined in accordance with the following formula:

$$V_T = (V_S + V_R) \cdot [(P_{RS} - P_A)/(P_C - P_A) - 1]$$

It is important to allow the temperature of the fluid media to equalize with the ambient temperature each time the above-described pressure changes occur before recording the pressure reading. This is necessary because the temperature of a gas rises when it is compressed. The change in temperature distorts the normal inverse relationship between volume and pressure. Typically, a 15-second delay is adequate for this purpose.

With reference to FIG. 2, measurement of the rate of consumption or production of the selected substance requires gas fraction determinations which are based upon the sample and reference signals generated by the appropriate sensor and are calculated by the processor 27 in a manner described below. At a minimum, these gas fraction determinations require from the sensor: a first reference fluid medium reading (R1), followed by a first sample fluid medium reading (T1), followed by a second reference fluid medium reading (R2), and a second sample fluid medium reading (T2). Each of the reference and sample gases is circulated through the sensors for an approximately equal period of time (t). The time required for one reference gas circulation period (t) and one sample gas circulation period (t) defines the test interval. In addition, a delay (d) is provided between initiation of one fluid medium circulation period (t) and initiation of signal readings from the sensors. This delay (d) is provided so that the newly introduced fluid medium has an opportunity to fill and replace the previous medium in the sensors.

In the calculations below, the values representing the sensor volume ($V_S$), net sample chamber volume ($V_T$), i.e. sample chamber volume minus sample volume, and known reference chamber volume ($V_R$) remain the same as set forth in the previous equations. If a gas analyzer consumes any of the selected component that it measures, "$O_S$" is set to the known consumption rate (ml/min), otherwise "O" is set to 0. The rate of consumption or production of the selected component by the sample is calculated in the following manner:

$c = .5 + d/t/2$
$X1 = \{V_R \cdot R1 + [V_R \cdot O_S \cdot t \cdot (1 - c)/(V_R + V_S)] + V_S \cdot T1 + V_S \cdot (1 - c) \cdot O_S \cdot t \cdot (V_T + V_S) + O_S \cdot c \cdot t\}/(V_R + V_S)$
$X2 = V_R/(V_R + V_S) + 1$
$X3 = (1 - c) \cdot V_S/(V_T + V_S)/(V_R + V_S)$
$X4 = \{V_S \cdot R2 + [V_S \cdot O_S \cdot (1 - c) \cdot t/(V_R + V_S)] + V_T \cdot T1 + [V_T \cdot O_S \cdot (1 - c) \cdot t/(V_T + V_S)] + O_S \cdot t \cdot c\}/(V_T + V_S)$
$X5 = V_T/(V_T + V_S) + 1$
$X6 = (2 \cdot V_T + V_S + V_S \cdot c)/(V_T + V_S)/(V_T + V_S)$
$X7 = [(T2 - X4)/X5] - [(R2 - X1)/X2]$
$X8 = X6/X5 - X3/X2$ Production (consumption) of selected component $= X7/X8/t$ (ml/min)

As may be noted, a separate calculation for sensor drift is not provided in the foregoing equations. Instead, sensor drift is accounted for by the manner in which the reference sample readings (R1, R2) are employed in these equation to determine the rate of production (consumption) of the selected component by the sample. Preferably, once carbon dioxide and oxygen production (consumption) rates have been calculated, a correction is made to the oxygen production (consumption) rate. Such a correction is desirable because production or consumption of carbon dioxide may cause changes in the oxygen concentrations in the measured gases, even when no oxygen has been added or removed from the system. If total volume changes as a result of production or consumption of carbon dioxide, but the amount of oxygen in that volume is the same, then the oxygen fraction, i.e. the relative quantity of oxygen divided by total volume, changes. The equation below gives the correction:

(corrected $O_2$ production or consumption = uncorrected $O_2$ production or consumption) + ($CO_2$ production or consumption. $O_2$ fraction)

This equation is an approximation of the Haldane transformation. The $O_2$ fraction is computed with the processor 27 by averaging the sample signals received by the processor from the oxygen sensor during any one sample circulation period (t), minus a delay (d), and by multiply the average signal by a known concentration/signal strength factor for the oxygen sensor. A corresponding correction of carbon dioxide production rates for changes in oxygen concentrations is typically unnecessary because the carbon dioxide fraction is normally very small.

Figure 5:
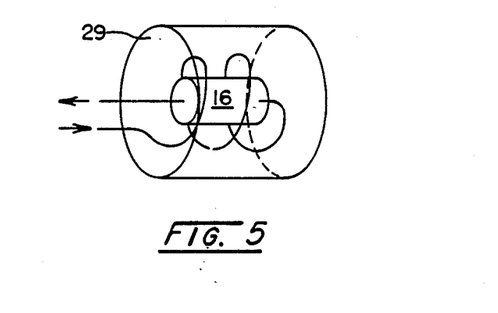
FIG. 5 is a diagram of the preferred components for regulating the temperature of the fluid media as they pass through the oxygen sensor.

As illustrated in FIG. 5, special steps may be taken to protect the oxygen sensor 16 from rapid temperature changes. In order for the drift compensation scheme set forth above to eliminate errors due to temperature change, the rate of temperature change of the oxygen sensor must remain fairly constant over a period of at least two sample intervals. Advantageously, the temperature of the fluid medium entering the oxygen sensor, typically a fuel cell, is stabilized by running it through a coil of tubing which is embedded in a block of wax 29. The fuel cell 16 is also embedded in the block of wax, and the block 29 is wrapped in insulating foam (not shown).

Figure 4:
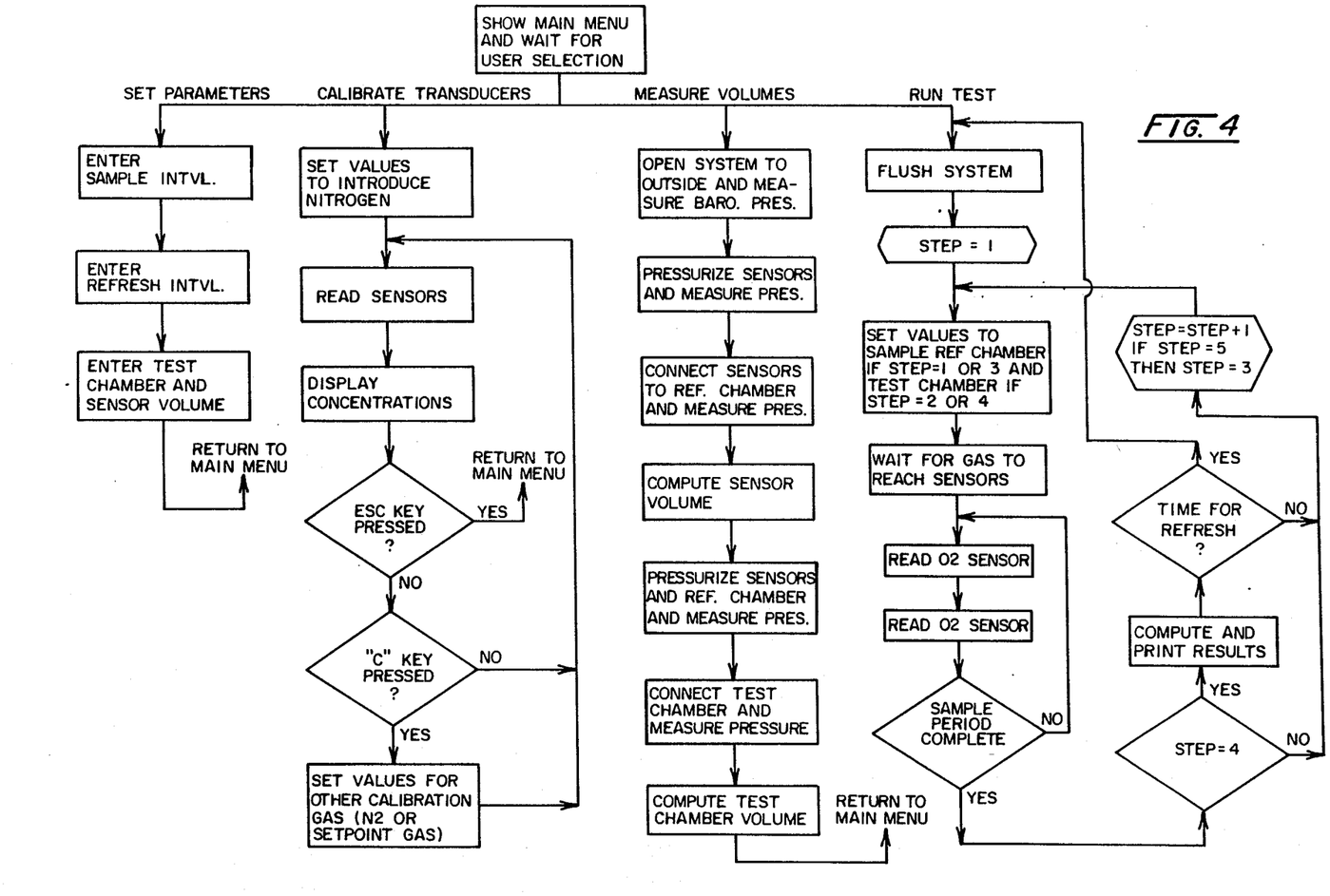
FIG. 4 is a flow chart of a computer program which controls various components of the subject respirometer.

The respirometer 10 is controlled by a processor comprising a microcomputer 27 and a control program (FIG. 4) which reads the sensor signals and pressure indicator signals, controls the duration of the various flushing, reference and sample circulation periods (t), delay period (d) and overall test intervals, calculates the oxygen and carbon dioxide consumption (production) rates, stores various data in memory and displays and/or prints the results. The program also allows the user to calibrate the carbon dioxide and oxygen sensors, add known values and select or override some of the time parameters, such as the test interval, the experiment duration, and the time period between flushing cycles.

The processor 27 communicates with the valves, gas sensors and pressure indicator using an interface 28. The sensors produce signal voltages which are indicative of the relative amounts or concentrations of oxygen and carbon dioxide in the reference and sample gases. These signal voltages are fed into two channels of an A/D converter within the interface. Twelve bits of A/D resolution has been found to be required to resolve sufficiently small voltage changes. The interface also contains several digital output control lines for controlling the intake and exhaust manifold valves (1–8). The valves are preferably of the solenoid type, so they are opened by the application of a voltage across the windings. When the digital output from the computer 27 goes high, a transistor in the interface 28 supplies the voltage required to change the position of the appropriate solenoid valve.

The computer reads the sensors continuously through the time when the reference and sample fluid media are being circulated, except for the delay time (d) described above. The sample and reference signals are converted to digital readings by the interface 28. All readings in one cycle of each fluid medium are averaged together, and the resulting average is multiplied by a known concentration/signal strength factor for the particular gas sensor to determine the average gas fraction of the selected component during that particular cycle. Noise in the readings is reduced by averaging, thereby giving more stable readings. The delay time (d) is computed by the program based on the flow rate of the gases through the sensors and the volume of gas in the sensors, and is made long enough to allow the newly circulated fluid medium to completely replace the previously circulated medium in the sensors. The computer program allows automatic and periodic flushing of the reference and sample chambers during the experiment. The composition of the fluid media in the chambers is likely to change substantially during the experiment due to mixing of the reference and sample gases and consumption or production of oxygen and carbon dioxide. By flushing the chambers, the gases are replaced. The flushing may be programmed to occur at periodic intervals, or it may be triggered by the oxygen or carbon dioxide levels crossing outside an acceptable range. The experiment is briefly interrupted during the flushing period and a subsequent settling period.

Figure 6:
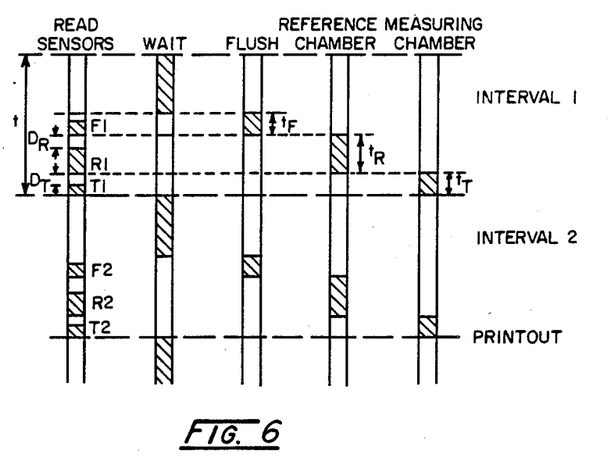
FIG. 6 is a diagram of an alternative timing sequence for circulating the fluid media and reading the sensors.

To achieve very high resolution in the measurement of oxygen consumption, longer testing intervals and a different method may be employed to minimize the effect of oxygen consumption by the oxygen sensor. The method differs mainly in two ways. First, the time intervals during which the reference and sample fluid media are circulated through the sensors may be different. The duration of each interval is chosen so that the percentage depletions of oxygen caused by the oxygen sensor in the reference and a sample gases are equal. Secondly, the fluid media are circulated through the sensors only long enough to make the measurement. The rest of the time the sensors are sitting idle or being flushed with outside air. The timing diagram for the long sample interval method is shown in FIG. 6 and consists of the following four steps: (1) a waiting or settling period during which all of the valves 1–8 are closed, the pumps are idle and the fluid media within the system are still; (2) a flushing period during which atmospheric air is flushed through the sensors and the gas fractions in the air are measured; (3) a reference assay period when the gas fractions of the selected components in the reference fluid medium are measured; and (4) a sample assay period when the gas fractions of the selected components in the sample fluid medium are measured. A first printout occurs after two test intervals, with succeeding printouts occurring on succeeding test intervals. As indicated in FIG. 5 and in the equations below, the following variables are used: $V_S$, $V_R$, $V_T$ = The respective volumes of the sensors, reference chamber (known), and sample chamber (net) (in ml). These quantities are determined or known as previously described. $t_T$, $t_R$, $t_F$ = Time intervals for circulation of the sample, reference and flushing gases, respectively, through the sensors (in minutes). $D_T$, $D_R$ = Delay periods between initiation of the sample and reference fluid media circulation, respectively, and initiation of sensor signal readings therefor (in minutes). t = Duration of one test interval which includes one settling period, as well as $t_T$, $t_R$ and $t_F$ (in minutes). R1, T1 = Gas fractions of the selected component in the reference and sample gases, respectively, during the first test interval (decimal fraction). F2, R2, T2 = Gas fractions of the selected component in the flushing, reference and sample gases, respectively, during the second test interval (decimal fraction). $O_S$ = Known rate of consumption of oxygen by the oxygen sensor (in ml/min). When carbon dioxide rates are calculated, $O_S$ = 0. $f_S$ = Rate of flow of sample fluid medium through the sensors (ml/min). The time interval ($t_T$) for circulating the sample gas through the sensors is preferably three (3) minutes and is substantially the same during each test interval. The delay period ($D_T$) between initiation of sample gas circulation and initiation of sensor signal readings by the processor preferably allows a quantity of sample gas approximately four times the volume of the sensors to flow therethrough and is calculated as follows:

$$D_T = 4 \cdot V_S / f_S$$

The time interval ($t_R$) for circulating the reference gas through the sensors is calculated as follows:

$$t_R = t_T(V_R + V_S)/(V_T + V_S)$$

The delay period ($D_R$) between initiation of reference gas circulation and initiation of sensor signal readings by the processor is calculated as follows:

$$D_R = D_T(V_R + V_S)/(V_T + V_S)$$

Preferably, the time interval ($t_F$) for circulating the flushing gas through the sensors is three (3) minutes and permits a quantity of air several times the volume of the sensors to pass therethrough.

Accordingly, a new calculation of the rate of production or consumption of the selected component by the sample proceeds as follows:

$$k = D_T/t/2 + .5$$
$$j = O_S \cdot t_T/(V_S + V_T)$$
$$X1 = \{{}^vV_R \cdot [R1 + (1 - k) \cdot j] + V_S \cdot F2\}/(V_R + V_S) + k \cdot j$$
$$X2 = \{-V_R \cdot t_R \cdot k - V_S \cdot [t - t_F \cdot (1 - k)]\}/(V_R + V_S) + t + k \cdot t_R$$
$$\text{Drift} = (R2 - X1)/X2$$
$$X3 = \{V_T \cdot [T1 + (1 - k) \cdot t_T \cdot O_S/(V_S + V_T)] + V_S \cdot [R2 + (1 - k) \cdot t_R \cdot O_S/(V_R + V_S)]\}/(V_T + V_S + O_S \cdot k \cdot t_T/(V_S + V_T)$$
$$X4 = [-V_T \cdot k \cdot t_T - V_S \cdot (t - t_R + k \cdot t_R)]/(V_S + V_T) + k \cdot t_T + t$$
$$X5 = \{[V_T \cdot (1 - k) \cdot t_T/(V_S + V_T)] + t - t_T\}/(V_S + V_T) + k \cdot t_T/(V_S + V_T)$$

Production or Consumption = (T2 − X3 − Drift.X4)/X5

A correction is preferably made to the oxygen production rate in the same manner as previously indicated in order to compensate for changes in carbon dioxide levels.

While several alternative embodiments of the present invention have been described and illustrated in some detail, the foregoing description and drawings are not intended to unduly limit or restrict the spirit of the invention nor the scope of the following claims.

We claim:

1. Apparatus for determining a rate at which a sample consumes or produces a selected component of a fluid medium, said apparatus comprising:
   (a) a reference chamber adapted to house a first quantity of a reference fluid medium;
   (b) a sample chamber adapted to house a sample and a second quantity of the reference fluid medium and wherein the sample interacts with said second quantity of the reference fluid medium to produce a sample fluid medium;
   (c) a sensor which generates a plurality of reference and sample signals, each of said reference and sample signals being substantially proportional in strength to a quantification of the selected component relative to the reference and sample fluid media, respectively;
   (d) means for alternately circulating the reference and sample fluid media from their respective chambers to the sensor and back to their respective chambers; and
   (e) a processor adapted to receive the reference signals and the sample signals generated by the sensor and to calculate the rate at which the sample consumes or produces the selected component in accordance with a formula which employs the reference signals to compensate for a drift in the sensor.

2. The apparatus according to claim 1, wherein a pressure indicator is connected in fluid communication with the sensor.

3. The apparatus according to claim 1, wherein a first sensor produces reference and sample signals each representing a carbon dioxide gas fraction in the reference and sample fluid media, respectively, and a second sensor produces reference and sample signals each representing an oxygen gas fraction in the reference and sample fluid media, respectively.

4. The apparatus according to claim 1, wherein the means for alternately circulating the reference and sample fluid media includes an intake manifold having a first valve connected to the sample chamber and a second valve connected to the reference chamber, a circulating pump downstream of the intake manifold, and an exhaust manifold downstream of the sensor, said exhaust manifold having a first valve connected to the sample chamber and a second valve connected to the reference chamber.

5. The apparatus according to claim 1, wherein pressure regulating means are provided for limiting pressure changes in the sample and fluid media within the sensor.

6. The apparatus according to claim 5, wherein the pressure regulating means includes a transducer generate a first variable signal indicative of the pressure within the sensor, a comparator which receives the first variable signal and generates a second signal, and a variable valve which increases and decreases a circulation of the reference and sample fluid media through the sensor in response to the second signal.

7. A method for determining a rate at which a sample consumes or produces a selected component of a fluid medium, said method comprising:
   (a) introducing a first quantity of a reference fluid medium into a reference chamber;
   (b) introducing a sample into a sample chamber;
   (c) introducing a second quantity of the reference fluid medium into the sample chamber for interaction with the sample to produce a sample fluid medium;
   (d) alternately circulating the reference and sample fluid media from their respective chambers to a sensor and back to their respective chambers;
   (e) generating a plurality of reference and sample signals with the sensor, each of said reference and sample signals being substantially proportional in strength to a quantification of the selected component relative to the reference and sample fluid media, respectively; and
   (f) calculating in a processor adapted to receive the reference and sample signals the rate at which the sample consumes or produces the selected component in accordance with a formula which employs the reference signals to compensate for a drift in the sensor.

8. The method according to claim 7 which includes establishing in the sensor and in the reference chamber a first pressure ($P_A$) which is substantially equal to an atmospheric air pressure; establishing in the sensor a second pressure ($P_S$) which is greater than said first pressure; establishing in said sensor and said reference chamber a third pressure ($P_T$) by equalizing the second pressure in the sensor and the first pressure in the reference chamber; generating first, second and third pressure signals indicative of said first, second and third pressures, respectively, with a pressure indicator in fluid communication with the sensor; transmitting said first, second and third pressure signals to the processor; providing a first volume signal indicative of a known ($V_R$) of the reference chamber; and calculating a quantity ($V_S$) indicative of a volume of the sensor in accordance with the following formula:

$$V_S = V_R / [(P_S - P_A)/(P_T - P_A) - 1].$$

9. The method according to claim 8, which includes establishing in the sensor, reference chamber and sample chamber the first pressure ($P_A$); establishing in the reference chamber and sensor a fourth pressure ($P_{RS}$) which is greater than said first pressure; establishing in said reference and sample chambers and in said sensor a fifth pressure ($P_C$) by equalizing the fourth pressure in the reference chamber and sensor and the first pressure in the sample chamber; generating first, fourth and fifth pressure signals indicative of said first, fourth and fifth pressure, respectively, with the pressure indicator; transmitting said first, fourth and fifth pressure signals to the processor; providing the first volume signal indicative of the known reference chamber volume ($V_R$) and a second volume signal indicative of the calculated sensor volume ($V_S$); and calculating a quantity ($V_T$) indicative of a net sample chamber volume in accordance with the following formula:

$$V_T = (V_S + V_R) \cdot [(P_{RS} - P_A)/(P_C - P_A) - 1].$$

10. The method according to claim 9, which includes selecting substantially equal time periods (t) for circulating the reference and sample media; selecting and providing a delay period (d) between an initiation of each of said time periods (t) and an initiation of readings by the processor of each of the respective reference and sample signals; providing a known signal strength factor of the sensor for the selected component of the reference and sample fluid media; calculating first (R1), second (T1), third (R2) and fourth (T2) quantifications of selected component with a first reference signal, a first sample signal, a second reference signal and a second sample signal, respectively, and with the known signal strength factor; providing a known value ($O_S$) indicative of a rate of consumption of the selected component by the sensor; providing the net sample chamber volume ($V_T$), the sensor volume ($V_S$) and the reference chamber volume ($V_R$); and calculating a rate of change in quantity of the selected component in accordance with the following formulae:

$$c = .5 + d/t/2,$$
$$X1 = \{V_R \cdot R1 + [V_R \cdot O_S \cdot t(1-c)/(V_R+V_S)] + V_S \cdot T1 +$$
$$V_S \cdot (1-c) \cdot O_S \cdot t \cdot (V_T+V_S) + O_S \cdot c \cdot t\}/(V_R+V_S),$$
$$X2 = V_R/(V_R+V_S) + 1,$$
$$X3 = (1-c) \cdot V_S/(V_T+V_S)/(V_R+V_S),$$
$$X4 = \{V_S \cdot R2 + [V_S \cdot O_S \cdot (1-c) \cdot t/(V_R+V_S)] + V_T \cdot T1 +$$
$$V_T \cdot O_S \cdot (1-c) \cdot t/(V_T+V_S) + O_S \cdot t \cdot c\}/(V_T+V_S),$$
$$X5 = V_T/(V_T+V_S) + 1,$$
$$X6 = (2 \cdot V_T + V_S + V_S \cdot c)/(V_T+V_S)/(V_T+V_S),$$
$$X7 = [(T2-X4)/X5] - [(R2-X1)/X2],$$
$$X8 = X6/X5 - X3/X2,$$

wherein the rate of change in quantity = $X7/X8/t$.

11. The method according to claim 10, wherein oxygen and carbon dioxide constitute first and second selected components of the reference and sample fluid medium and wherein the method further includes calculating a corrected rate of change in quantity of oxygen in accordance with the following formula:

Rate $O_2$ cor. = rate $O_2$ uncor. + (rate $CO_2 \times T1$), where "Rate $O_2$ cor." means the corrected rate of change in quantity of oxygen;

"Rate $O_2$ uncor." means the rate of change in quantity of oxygen derived from the formulae set forth in claim 10;

"Rate $CO_2$" means the rate of change in quantity of carbon dioxide derived from the formulae set forth in claim 10; and "T1" means the second quantification of oxygen determined from the first sample signal and the known signal strength factor, as set forth in claim 10.

12. The method according to claim 9, which includes circulating a flushing fluid medium through the sensor prior to circulating the reference and sample fluid media; providing a settling period to circulating the flushing fluid medium; and generating a plurality of flushing signals with the sensor, each of said flushing signals being substantially proportional in strength to a relative quantity of the selected component in the flushing fluid medium.

13. The method according to claim 12, which includes selecting a first time period for the settling period; selecting a second time period ($t_F$) for circulating the flushing fluid medium; selecting a third time period ($t_T$) for circulating the sample fluid medium; calculating a fourth time period ($t_R$) for circulating the reference fluid medium in accordance with the following formula:

$$t_R = t_T(V_R + V_S)/(V_T + V_S);$$

calculating a test interval (t) by adding the first, second, third and fourth time periods; determining a rate of flow ($f_S$) of the sample fluid medium with a flow meter in fluid communication with the sensor; calculating and providing a first delay ($D_R$) between an initiation of reference fluid medium circulation and an initiation of readings by the processor of the reference signals in accordance with the following formula:

$$D_R = [(4 \cdot V_S/f_S) \cdot (V_R + V_S)]/(V_T + V_S);$$

calculating and providing a second delay ($D_T$) between an initiation of sample fluid medium circulation and an initiation of readings by the processor of the sample signals in accordance with the following formula:

$$D_T = 4 \cdot V_S/f_S;$$

providing a known signal strength factor of the sensor for the selected component of the reference sample and flushing fluid media; calculating first (R1), second (T1), third (F2), fourth (R2), and fifth (T2) quantifications of the selected component with a first reference signal, a first sample signal, a second flushing signal, a second reference signal and a second sample signal, respectively, and with the known signal strength factor; providing a known value ($O_S$) indicative of a rate of consumption of the selected component by the sensor; providing the net sample chamber volume ($V_T$), the sensor volume ($V_S$), and the reference chamber volume ($V_R$); and calculating a rate of change in quantity of the selected component in accordance with the following formulae:

$$k = D_T/t/2 + .5,$$
$$j = O_S \cdot t_T/(V_S + V_T),$$

-continued $$X1 = \{V_R \cdot [R1 + (1-k) \cdot j] + V_S \cdot F2\}/(V_R + V_S) + k \cdot j,$$
$$X2 = \{-V_R \cdot t_R \cdot k - V_S \cdot [t - t_F \cdot (1-k)]\}/(V_R + V_S) + t + k \cdot t_R$$

Drift = $(R2 - X1)/X2$, $$X3 = \{V_T \cdot [T1 + (1-k) \cdot t_T \cdot O_S/(V_S + V_T)] + V_S \cdot [R2 + (1-k) \cdot t_R \cdot O_S/(V_R + V_S)]\}/(V_T + V_S + O_S \cdot k \cdot t_T/(V_S + V_T),$$

$$X4 = [-V_T \cdot k \cdot t_T - V_S \cdot (t - t_R + k \cdot t_R)]/(V_S + V_T) + k \cdot t_T + t,$$

$$X5 = \{[V_T \cdot (1-k) \cdot t_T/(V_S + V_T)] + t - t_T\}/(V_S + V_T) + k \cdot t_T/(V_S + V_T),$$

wherein the rate of change in quantity = $(T2 - X3 - \text{Drift} \cdot X4)/X5$.

14. The method according to claim 13, wherein oxygen and carbon dioxide constitute first and second selected components of the flushing, sample and reference fluid media and wherein the method further includes calculating a corrected rate of change in quantity of oxygen in accordance with the following formula:

Rate $O_2$ cor. = rate $O_2$ uncor. + (rate $CO_2 \times T1$), where "Rate $O_2$ cor." means the corrected rate of change in quantity of oxygen;
"Rate $O_2$ uncor." means the rate of change in quantity of oxygen derived from the formulae set forth in claim 13;
"Rate $CO_2$" means the rate of change in quantity of carbon dioxide derived from the formulae set forth in claim 13; and
"T1" means the second quantification of oxygen determined from the first sample signal and the known signal strength factor, as set forth in claim 13.

* * * * *

UNITED STATES PATENT AND TRADEMARK OFFICE
CERTIFICATE OF CORRECTION

PATENT NO. : 4,947,339

DATED : August 7, 1990

INVENTOR(S) : Nennerfelt et al.

It is certified that error appears in the above-identified patent and that said Letters Patent is hereby corrected as shown below:

Title page, item [19] should read --Nennerfelt et al--

Item [75] the order of names should read --  Leif B. Nennerfelt and Jan Czekajewski --

Signed and Sealed this

Twentieth Day of August, 1991

Attest:

HARRY F. MANBECK, JR.

*Attesting Officer*          *Commissioner of Patents and Trademarks*